United States Patent [19]
McAtee et al.

[11] Patent Number: 5,916,575
[45] Date of Patent: *Jun. 29, 1999

[54] CLEANING PRODUCTS

[75] Inventors: David Michael McAtee, Mason; Robert Bao Kim Ha, Milford; Timothy John Fowler, Cincinnati, all of Ohio

[73] Assignee: The Procter & Gamble Company, Cincinnati, Ohio

[*] Notice: This patent is subject to a terminal disclaimer.

[21] Appl. No.: 08/789,358

[22] Filed: Jan. 27, 1997

[51] Int. Cl.⁶ .............................. C11D 17/00; A61K 7/48; A61K 7/50
[52] U.S. Cl. ..................... 424/401; 510/130; 510/159; 510/417; 510/461; 514/846
[58] Field of Search .............................. 424/401; 510/119, 510/129, 130, 136, 137, 138, 159, 417, 461, 481; 514/846

[56] References Cited

U.S. PATENT DOCUMENTS

| | | | |
|---|---|---|---|
| 4,990,501 | 2/1991 | Imrie et al. | 514/54 |
| 5,160,738 | 11/1992 | Macaulay et al. | 424/401 |
| 5,179,128 | 1/1993 | Lyle et al. | 252/165 |
| 5,306,444 | 4/1994 | Kitamura et al. | 510/490 |
| 5,306,516 | 4/1994 | Letton et al. | 426/531 |
| 5,372,744 | 12/1994 | Kamegai et al. | 252/174.17 |
| 5,419,925 | 5/1995 | Seiden et al. | 426/611 |
| 5,464,554 | 11/1995 | Gu et al. | 252/121 |
| 5,683,683 | 11/1997 | Scafidi | 424/70.19 |
| 5,688,752 | 11/1997 | Turner | 510/159 |
| 5,716,920 | 2/1998 | Glenn, Jr. et al. | 510/159 |
| 5,804,540 | 9/1998 | Tsaur et al. | 510/135 |
| 5,834,516 | 11/1998 | O'Lenick Jr. | 514/563 |

FOREIGN PATENT DOCUMENTS

| | | | |
|---|---|---|---|
| A-0458600 | 11/1991 | European Pat. Off. | A61K 7/00 |
| A-0466410 A2 | 1/1992 | European Pat. Off. | A61K 7/48 |
| A-0519727 | 12/1992 | European Pat. Off. | A61K 7/48 |
| A-0587288 | 3/1994 | European Pat. Off. | A61K 7/48 |
| A-0783871A1 | 7/1997 | European Pat. Off. | A61B 17/39 |
| 61143497 | 12/1984 | Japan | C07F 9/09 |
| 2297762 | 8/1996 | United Kingdom | C11D 1/74 |
| 2297975 | 8/1996 | United Kingdom | C11D 3/20 |
| WO 93/09761 | 5/1993 | WIPO | A61K 7/50 |
| WO 95/17163 | 6/1995 | WIPO | A61K 7/50 |
| WO 96/03974 | 2/1996 | WIPO | A61K 7/48 |
| WO 96/12000 | 4/1996 | WIPO | C11D 1/65 |
| WO 96/17050 | 6/1996 | WIPO | C11D 3/50 |
| WO 96/17590 | 6/1996 | WIPO | A61K 7/48 |
| WO 96/17591 | 6/1996 | WIPO | A61K 7/48 |
| Wo 96/17592 | 6/1996 | WIPO | A61K 7/50 |
| WO 96/25144 | 8/1996 | WIPO | A61K 7/48 |
| WO 96/28139 | 9/1996 | WIPO | A61K 7/50 |
| WO 96/28140 | 9/1996 | WIPO | A61K 7/50 |
| WO 96/28144 | 9/1996 | WIPO | A61K 31/00 |
| WO 96/37595 | 11/1996 | WIPO | C11D 3/22 |

OTHER PUBLICATIONS

ASTM Designation: E 70–90: "Standard Test Method for pH of Aqueous Solutions with the Glass Electrode", published Mar. 1990.

ASTM Designation: D 971–91: "Standard Test Method for Interfacial Tension of Oil Against Water by The Ring Method", published Nov. 1991.

Max Factor Cleanse–A–Gel®, Max Factor & Co., Hollywood, CA, Code 3641–11.

Dawn Dishwashing Detergent®, 1996 Procter & Gamble, Cincinnati, OH.

Phisoderm Daily Skin Cleanser & Conditioner®, Distributed by Chattem, Inc., Chattanooga, TN.

Liquid Neutrogena Facial Cleansing Formula®, Neutrogena Corporation, Los Angeles, CA.

Oil of Olay Moisturizing Body Wash®, 1996 Procter & Gamble, Cincinnati, OH.

Oil of Olay Daily Renewal Cleansing Milk® (Europe) Nov. 1996.

*Primary Examiner*—Robert H. Harrison
*Attorney, Agent, or Firm*—Stephen T. Murphy; Armina E. Matthews; George W. Allen

[57] ABSTRACT

The present invention relates to a non-emulsified personal cleansing composition comprising a cleansing component further comprising a lathering surfactant and water; and an insoluble skin conditioning component, wherein the insoluble skin conditioning component has an interfacial tension index of less than about 150% in the cleansing component. The invention also encompasses methods for cleansing and conditioning the skin or hair using these products.

22 Claims, No Drawings

CLEANING PRODUCTS

TECHNICAL FIELD

The present invention relates to compositions for personal cleansing in the form of non-emulsified oil, surfactant and water dispersions. These dispersions provide more efficient delivery of both the water-insoluble oils and water soluble cleansing ingredients to the skin than is provided by most emulsion products. Therefore, these compositions have the advantage of providing improved cleansing efficacy without irritating the skin or leaving the skin feeling tight or dry.

BACKGROUND OF THE INVENTION

Personal cleansing products have traditionally been marketed in a variety of forms such as bar soaps, creams, lotions, and gels. These cleansing formulations have attempted to satisfy a number of criteria to be acceptable to consumers. In order to be acceptable to consumers, a product must exhibit good cleansing properties, must exhibit good lathering characteristics, must be mild to the skin and preferably should provide a moisturizing benefit to the skin. Ideal personal cleansers should gently cleanse the skin or hair, cause little or no irritation, and not leave the skin or hair overly dry after frequent use.

These traditional forms of personal cleansing products have the inherent problem of balancing cleansing efficacy against delivering a conditioning benefit. One solution to this problem is for the consumer to use separate cleansing and conditioning products. This is not always convenient or practical and many consumers would prefer to use a single product which can both cleanse and condition the skin or hair. However, in typical cleansing compositions, the conditioning ingredients are difficult to incorporate because many conditioners are incompatible with the surfactants, resulting in an undesirable non-homogenous mixture.

To obtain a stable homogeneous mixture of surfactants and conditioning agents, two-phase emulsions have been formulated. The oil based conditioning agents are dispersed in the oil phase and the surfactant cleansing system is dispersed in the water phase. This results in an aesthetically pleasing uniform emulsion mixture, but can result in poor deposition of conditioning ingredients, because the conditioners are emulsified and not necessarily efficiently released during cleansing.

Also, most traditional skin conditioning oils have the disadvantage of suppressing lather generation. It is known that the addition of an oil to a surfactant solution results in a increase in interfacial tension of the solution due to the fact that the surfactant molecules are tied up with the oil at the oil-water interface of the emulsion. The increased interfacial tension decreases the lathering and cleaning ability of the surfactant. Lather suppression is a problem because many consumers seek cleansing products that provide a rich, creamy, and generous lather.

One way to provide cleansing compositions which incorporate both insoluble conditioning components and water-soluble cleansing components without the disadvantages particularly associated with the emulsion form would be therefore, to develop a non-emulsified form of cleansing composition with insoluble conditioners and water-based cleansers.

Applicants have found that, surprisingly, personal cleansing products which contain both insoluble skin conditioning ingredients and a cleaning surfactant can be formulated without forming an emulsion. Since no emulsion is formed, the interfacial tension of the surfactant solution remains low and the lathering and cleansing benefits of the surfactant are maintained. Without being limited by theory it is believed that since the insoluble skin conditioning ingredients are dispersed in the composition, they are more efficiently deposited to the skin, providing conditioning benefits. Also, since the insoluble skin conditioning ingredients are dispersed in the composition without dramatically increasing the interfacial tension of the cleansing components, the cleansing and lathering benefits of the cleansing component are not negatively affected.

The present invention relates to non-emulsified personal cleansing compositions which consist of a lathering surfactant based cleansing component and an insoluble skin conditioning component which does not increase the interfacial tension of the cleansing component by more than 150%. The compositions provide improved cleansing and skin conditioning benefits over traditional oil-in-water emulsion cleansers.

SUMMARY OF THE INVENTION

The present invention relates to a non-emulsified personal cleansing composition comprising:

A. from about 35% to about 99.9%, by weight of the personal cleansing composition, of a cleansing component comprising:
  i. from about 5% to about 74.5%, by weight of the personal care composition, of a lathering surfactant; and
  ii. from about 25% to about 89.9%, by weight of the personal care composition, of water; and
B. from about 0.1% to about 65%, by weight of the personal cleansing composition, of an insoluble skin conditioning component;

wherein the insoluble skin conditioning component has an interfacial tension index of less than about 150% in the cleansing component.

In one embodiment of the present invention, the insoluble skin conditioning component within the non-emulsified personal cleansing composition comprises a solid polyol carboxylic acid ester and an insoluble skin conditioning oil wherein the ratio of the amount of the solid polyol carboxylic acid ester to the amount of insoluble skin conditioning oil is from about 20:80 to about 100:0.

The present invention also relates to methods for cleansing and conditioning the skin or hair and to methods for removing make-up from skin with the personal cleansing products described herein.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

DETAILED DESCRIPTION OF THE INVENTION

The non-emulsified personal cleansing compositions of the present invention are highly efficacious for cleansing the skin or hair, yet provide good skin conditioning.

I. THE NON-EMULSIFIED PERSONAL CLEANSING COMPOSITIONS

The term "non-emulsified personal cleansing composition" as used herein means a composition suitable for application to the human skin or hair for the purpose of removing dirt, make-up, oil and the like, which incorporates both insoluble and water-soluble ingredients, but which does not exhibit separate oil and water phases in the composition at 25° C.

The personal care products of the present invention comprise the following essential components.

A. Cleansing Component

The term "cleansing component" used herein means a set of ingredients, which are generally, but not necessarily water soluble, added to the compositions of the present invention for the purpose of cleaning dirt, oil, make-up and the like or for the purpose of adding lather benefits of the composition. The products of the present invention comprise from about 35% to about 99.9%, preferably from about 50% to about 99%, more preferably from about 60% to about 98%, and even more preferably from about 70 to about 97%, based on the weight of the personal cleansing composition, of the cleansing component.

The cleansing component of the personal cleansing compositions of the present invention comprise a lathering surfactant and water.

1. LATHERING SURFACTANT

The non-emulsified personal cleansing compositions of the present invention comprise from about 5% to about 74.5%, preferably from about 7.5% to about 50%, and more preferably from about 10% to about 25%, based on the weight of the personal cleansing composition, of a lathering surfactant.

By a "lathering surfactant" it is meant a surfactant, which when combined with water and mechanically agitated generates a foam or lather. Preferably, these surfactants should be mild, which means that these surfactants provide sufficient cleansing or detersive benefits but do not overly dry the skin or hair, and yet meet the lathering criteria described above. A lathering surfactant is further defined herein as a synthetic surfactant or mixture of surfactants which has an equilibrium surface tension of between 15 and 50 dynes/centimeter, more preferably between 20 and 45 dynes/centimeter as measured at the critical miscelle concentration at 25C°. Some surfactant mixtures can have a surface tension lower than any of its components.

The term "mild" as used herein in reference to the lathering surfactants and products of the present invention means that the products of the present invention demonstrate skin mildness comparable to a mild alkyl glyceryl ether sulfonate (AGS) surfactant based synthetic bar, i.e. synbar. Methods for measuring mildness, or inversely the irritancy, of surfactant containing products, are based on a skin barrier destruction test. In this test, the milder the surfactant, the lesser the skin barrier is destroyed. Skin barrier destruction is measured by the relative amount of radio-labeled (tritium labeled) water (3H—H$_2$O) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, to Small et al., issued Jun. 16, 1987, which are both incorporated by reference herein in their entirety. Other testing methodologies for determining surfactant mildness well known to one skilled in the art can also be used.

A wide variety of lathering surfactants are useful herein and include those selected from the group consisting of anionic lathering surfactants, nonionic lather surfactants, amphoteric lathering surfactants, and mixtures thereof.

Cationic surfactants can also be used as optional components, provided they do not negatively impact the overall lathering characteristics of the required, lathering surfactants.

Anionic Lathering Surfactants

Nonlimiting examples of anionic lathering surfactants useful in the compositions of the present invention are disclosed in McCutcheon's, *Detergents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975.

A wide variety of anionic lathering surfactants are useful herein. Nonlimiting examples of anionic lathering surfactants include those selected from the group consisting of sarcosinates, sulfates, isethionates, taurates, phosphates, carboxylates, and mixtures thereof. Amongst the isethionates, the alkoyl isethionates are preferred, and amongst the sulfates, the alkyl and alkyl ether sulfates are preferred. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanolamine. Another suitable class of anionic surfactants are the water-soluble salts of the organic, sulfuric acid reaction products of the general formula:

wherein R$_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates, nonlimiting examples of which include sodium lauroyl sarcosinate, sodium cocoyl sarcosinate, and ammonium lauroyl sarcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Other anionic materials include the carboxylates, nonlimiting examples of which include sodium laureth carboxylate, sodium lauroyl carboxylate, sodium cocoyl carboxylate, and ammonium lauroyl carboxylate.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety.

Nonlimiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl sarcosinate, sodium laureth carboxylate, and mixtures thereof.

Especially preferred for use herein is sodium laureth sulfate and sodium laureth carboxylate.

Nonionic Lathering Surfactants

Nonlimiting examples of nonionic lathering surfactants for use in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonionic lathering surfactants useful herein include those selected from the group consisting of alkyl glucosides, alkyl polyglucosides, polyhydroxy fatty acid amides, alkoxylated fatty acid esters, sucrose esters, amine oxides, and mixtures thereof.

Alkyl glucosides and alkyl polyglucosides are useful herein, and can be broadly defined as condensation products of long chain alcohols, e.g. $C_{8-30}$ alcohols, with sugars or starches or sugar or starch polymers, i.e., glycosides or polyglycosides. These compounds can be represented by the formula $(S)_n$—O—R wherein S is a sugar moiety such as glucose, fructose, mannose, and galactose; n is an integer of from about 1 to about 1000, and R is a $C_{8-30}$ alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a $C_{8-20}$ alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polyhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R_2CO$— moiety is derived from coconut oil fatty acids). Processes for making compositions containing polyhydroxy fatty acid amides are disclosed, for example, in U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyldecylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

Nonlimiting examples of preferred nonionic surfactants for use herein are those selected form the group consisting of $C_8$–$C_{14}$ glucose amides, $C_8$–$C_{14}$ alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Nonlimiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the $RCONH(CH_2)_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Mirataine CBS from Rhone-Poulenc).

Preferred for use herein are amphoteric surfactants having the following structure:

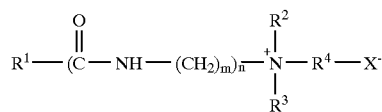

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are $CH_3$; X is selected from the group consisting of $CO_2$, $SO_3$ and $SO_4$; $R^4$ is selected from the group consisting of saturated or unsaturated, straight or branched chain alkyl, unsubstituted or monosubstituted with hydroxy, having from 1 to about 5 carbon atoms. When X is $CO_2$, $R^4$ preferably has 1 or 3 carbon atoms, more preferably 1 carbon atom. When X is $SO_3$ or $SO_4$, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine)

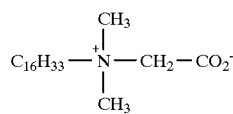

Cocamidopropylbetaine

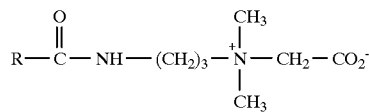

wherein R has from about 9 to about 13 carbon atoms

Cocamidopropyl hydroxy sultaine

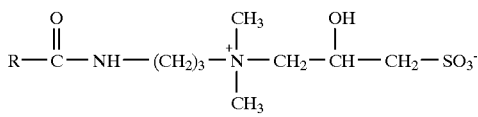

wherein R has from about 9 to about 13 carbon atoms.

Examples of other useful amphoteric surfactants are alkyliminoacetates, and iminodialkanoates and aminoalkanoates of the formulas $RN[CH_2)_mCO_2M]_2$ and $RNH(CH_2)_mCO_2M$ wherein m is from 1 to 4, R is a $C_8$–$C_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include amphoteric phosphates, such as coamidopropyl PG-dimonium chloride phosphate (commercially available as Monaquat PTC, from Mona Corp.). Also useful are amphoacetates such as disodium lauroamphodiacetate, sodium lauroamphoacetate, and mixtures thereof.

Preferred lathering surfactants for use herein are the following, wherein the anionic lathering surfactant is selected from the group consisting of ammonium lauroyl sarcosinate, sodium trideceth sulfate, sodium lauroyl sarcosinate, ammonium laureth sulfate, sodium laureth sulfate, ammonium lauryl sulfate, sodium lauryl sulfate, ammonium cocoyl isethionate, sodium cocoyl isethionate, sodium lauroyl isethionate, sodium cetyl sulfate, sodium laureth carboxylate, and mixtures thereof; wherein the nonionic lathering surfactant is selected from the group consisting of lauramine oxide, cocoamine oxide, decyl polyglucose, lauryl polyglucose, sucrose cocoate, $C_{12-14}$ glucosamides, sucrose laurate, and mixtures thereof; and wherein the amphoteric lathering surfactant is selected from the group consisting of disodium lauroamphodiacetate, sodium lauroamphoacetate, cetyl dimethyl betaine, cocoamidopropyl betaine, cocoamidopropyl hydroxy sultaine, and mixtures thereof.

2. WATER

The compositions of the present invention comprise from about 25% to about 94.9%, preferably from about 35% to about 90%, more preferably from about 40% to about 70% water. The level of water within these ranges which should be employed depends upon the form and the rheology of the product desired.

B. Insoluble Skin Conditioning Component

The non-emulsified personal cleansing compositions of the present invention also comprise an insoluble skin conditioning component which is useful for providing a conditioning benefit to the skin or hair following the use of the product. The insoluble conditioning agent comprises from about 0.1% to about 65%, preferably from about 1% to about 50%, more preferably from about 2% to about 25%, and most preferably from about 3% to about 10%, by weight of the personal cleansing composition.

By the term "insoluble" it is meant that the ingredient described as such is not soluble in water at 25° C.

The insoluble skin conditioning component is selected the group consisting of insoluble skin conditioning oils, insoluble skin conditioning solids, and mixtures thereof, provided that the insoluble skin conditioning component has a interfacial tension index of less than or equal to 150%, preferably less than or equal to 100, and more preferably less than or equal to 75%.

The interfacial tension index used herein is defined as a measure of the difference in interfacial tension (IFT) between a liquid and that same liquid after an additional ingredient has been added, as measured by ASTM Designation: D 971-91, "Standard Test Method for Interfacial Tension of Oil Against Water by the Ring Method", incorporated by reference in its entirety. Therefore, the interfacial tension index is represented by the following equation:

$$\text{Interfacial Tension Index} = \frac{\text{IFT of liquid and ingredient} - \text{IFT of liquid}}{\text{IFT of liquid only}} \times 100\%$$

In the composition of the present invention the interfacial tension index is the measure of the increase in interfacial tension caused by the addition of the insoluble skin conditioning agent to the cleansing component.

1. INSOLUBLE SKIN CONDITIONING OILS

The non-emulsified personal cleansing care compositions of the present invention comprise less than or equal to 80%, by weight of the insoluble skin conditioning component, of an insoluble skin conditioning oil. Nonlimiting examples of conditioning agents useful as insoluble skin conditioning oils include those selected from the group consisting of mineral oil, petrolatum, $C_7$–$C_{40}$ branched chain hydrocarbons, $C_1$–$C_{30}$ alcohol esters of $C_1$–$C_{30}$ carboxylic acids, $C_1$–$C_{30}$ alcohol esters of $C_2$–$C_{30}$ dicarboxylic acids, monoglycerides of $C_1$–$C_{30}$ carboxylic acids, diglycerides of $C_1$–$C_{30}$ carboxylic acids, triglycerides of $C_1$–$C_{30}$ carboxylic acids, ethylene glycol monoesters of $C_1$–$C_{30}$ carboxylic acids, ethylene glycol diesters of $C_1$–$C_{30}$ carboxylic acids, propylene glycol monoesters of $C_1$–$C_{30}$ carboxylic acids, propylene glycol diesters of $C_1$–$C_{30}$ carboxylic acids, liquid polyol carboxylic acid esters and polyesters including $C_1$–$C_{30}$ carboxylic monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol $C_4$–$C_{20}$ alkyl ethers, di $C_8$–$C_{30}$ alkyl ethers, and mixtures thereof.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p.415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, Drug. Cosmet. Ind., 89, 36–37, 76, 78–80, 82 (1961); and International Cosmetic Ingredient Dictionary, Fifth Edition, vol. 1, p. 537 (1993).

Straight and branched chain hydrocarbons having from about 7 to about 40 carbon atoms are useful herein. Nonlimiting examples of these hydrocarbon materials include dodecane, isododecane, squalane, cholesterol, hydrogenated polyisobutylene, docosane (i.e. a $C_{22}$ hydrocarbon), hexadecane, isohexadecane (a commercially available hydrocarbon sold as Permethyl® 101A by Presperse, South Plainfield, N.J.). Also useful are the $C_7$–$C_{40}$ isoparaffins, which are $C_7$–$C_{40}$ branched hydrocarbons.

Also useful are $C_1$–$C_{30}$ alcohol esters of $C_1$–$C_{30}$ carboxylic acids and of $C_2$–$C_{30}$ dicarboxylic acids, including straight and branched chain materials as well as aromatic derivatives. Also useful are esters such as monoglycerides of $C_1$–$C_{30}$ carboxylic acids, diglycerides of $C_1$–$C_{30}$ carboxylic acids, triglycerides of $C_1$–$C_{30}$ carboxylic acids, ethylene glycol monoesters of $C_1$–$C_{30}$ carboxylic acids, ethylene glycol diesters of $C_1$–$C_{30}$ carboxylic acids, propylene glycol monoesters of $C_1$–$C_{30}$ carboxylic acids, and propylene glycol diesters of $C_1$–$C_{30}$ carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various liquid polyol carboxylic acid esters, including $C_1$–$C_{30}$ monoesters and polyesters of sugars and related materials. These esters are derived from a sugar or polyol moiety and one or more carboxylic acid moieties. Examples of liquid esters include glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Other preferred materials include cottonseed oil or soybean oil fatty acid esters of sucrose. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Nonvolatile silicones such as polydialkylsiloxanes, polydiarylsiloxanes, and polyalkarylsiloxanes are also useful oils. These silicones are disclosed in U.S. Pat. No. 5,069,897, to Orr, issued Dec. 3, 1991, which is incorporated by reference herein in its entirety. The polyalkylsiloxanes correspond to the general chemical formula $R_3SiO[R_2SiO]_xSiR_3$ wherein R is an alkyl group (preferably R is methyl or ethyl, more preferably methyl) and x is an integer up to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful herein include Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer up to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also useful herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are $C_4$–$C_{20}$ alkyl ethers of polypropylene glycols, $C_1$–$C_{20}$ carboxylic acid esters of polypropylene glycols, and di-$C_8$–$C_{30}$ alkyl ethers. Nonlimiting examples of these materials include PPG-14 butyl ether, PPG-15 stearyl ether,, dioctyl ether, dodecyl octyl ether, and mixtures thereof.

2. INSOLUBLE SKIN CONDITIONING SOLIDS

Nonlimiting examples of conditioning agents useful as insoluble skin conditioning solids include various solid polyol carboxylic acid esters, including $C_1$–$C_{30}$ monoesters and polyesters of sugars and related materials. These solid polyol carboxylic acid esters are derived from a sugar or polyol moiety and one or more carboxylic acid moieties. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of esterification is 7–8, and in which the fatty acid moieties are $C_{18}$ mono- and/or di-unsaturated and behenic, in a molar ratio of unsaturates-:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985; all previously incorporated by reference herein.

In a preferred embodiment of the present invention, the skin conditioning component comprises a combination of insoluble skin conditioning oils and insoluble skin conditioning solids. In an especially preferred embodiment of the present invention the skin conditioning component comprises a combination of insoluble skin conditioning oil and solid carboxylic acid ester as the insoluble skin conditioning solid. The weight ratio of solid polyol carboxylic acid ester to insoluble skin conditioning oil is from about 20:80 to about 100:0 preferably 30:70 to about 99:1, more preferably from about 35:65 to about 90:10, and even more preferably from about 35:65 to about 60:40.

Not being limited by theory, it is believed that the insoluble skin conditioning solid adsorbs the insoluble skin conditioning oil to a point where the surfactant molecules do not chemically respond to the oil. Therefore, no surfactant molecules are tied up attempting to emulsify the oils and no change in interfacial tension occurs. The combination of insoluble skin conditioning oil and solid remains dispersed in the cleansing component and can be efficiently deposited on the skin or hair upon application.

C. Optional Ingredients

The compositions of the present invention can comprise a wide range of optional ingredients. The *CTFA Cosmetic Ingredient Handbook,* Second Edition, 1992, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference. Examples of these functional classes include: abrasives, anti-acne agents, anticaking agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, and suspending agents), suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

II. METHODS OF MANUFACTURE

The non-emulsified personal cleansing compositions of the present invention are made via art recognized techniques for the various forms of personal cleansing products.

III. METHODS OF USING THE NON-EMULSIFIED PERSONAL CLEANSING COMPOSITION

The non-emulsified personal cleansing compositions of the present invention are useful for personal cleansing, especially for cleansing of the face and neck areas. Typically, a suitable or effective amount of the cleansing composition is applied to the area to be cleansed. Alternatively, a suitable amount of the cleansing composition can be applied via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the product can be used alone and wiped-off from the skin using a pad, cotton ball, tissue, or other like device. The cleansing process is typically a two-step process involving application of the product followed either by rinsing of the product with water or wiping without the use of water. Generally, an effective amount of product to be used will depend upon the needs and usage habits of the individual. Typical amounts of the present compositions useful for cleansing range from about 0.5 mg/cm$^2$ to about 25 mg/cm$^2$ of skin area to be cleansed.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

Examples 1–4

Bodywash Products

| | Ex. 1 | Ex. 2 | Ex. 3 | Ex. 4 |
|---|---|---|---|---|
| Phase A | | | | |
| Water | 62.72 | 65.72 | 59.72 | 63.72 |
| Disodium EDTA | 0.20 | 0.20 | 0.20 | 0.20 |
| Phase B | | | | |
| Glycerine | 3.00 | 3.00 | 3.00 | 3.00 |
| Polyquaternium 10 | 0.40 | 0.40 | 0.40 | 0.40 |
| Phase C | | | | |
| Sodium/Magnesium Laureth-3-3.6 Sulphate | 12.00 | 12.00 | 12.00 | 12.00 |
| Cocamide MEA | 2.80 | 2.80 | 2.80 | 2.80 |
| Sodium Lauraphoacetate | 6.00 | 6.00 | 6.00 | 6.00 |
| Myristic Acid | 1.60 | 1.60 | 1.60 | 1.60 |
| Magnesium Sulphate Hepta Hydrate | 0.30 | 0.30 | 0.30 | 0.30 |
| Trihydroxystearin | 0.50 | 0.50 | 0.50 | 0.50 |
| PEG-6 Caprylic/Capric Triglycerides | 3.00 | — | — | — |
| Phase D | | | | |
| Sucrose Polyesters of Cottonate Fatty Acid | 3.00 | — | — | — |
| Sucrose Polyesters of Behenate Fatty Acid | 3.00 | 2.00 | 4.00 | 2.00 |
| Petrolatum | — | 4.00 | 8.00 | — |
| Mineral Oil | — | — | — | 6.00 |
| Phase E | | | | |
| DMDM Hydantoin | 0.08 | 0.08 | 0.08 | 0.08 |
| Citric Acid | 1.40 | 1.40 | 1.40 | 1.40 |
| | 100.00 | 100.00 | 100.00 | 100.00 |

The insoluble skin conditioning component of these compositions have an interfactial tension index of 150% or less.

Method of manufacture:
1. In a stainless steel vessel combine ingredients in phase A.
2. In a separate vessel combine ingredients in phase B until a homogeneous mixture is formed.
3. Add Phase B to phase A.
4. Add phase C ingredients to phase A vessel while heating to 85° C.
5. In a separate vessel, combine ingredients in phase D. Add to phase A vessel.
6. Begin cooling. When temperature reaches 30° C., add ingredients in phase E.

Examples 5–8

Facewash Products

| | Ex. 5 | Ex. 6 | Ex. 7 | Ex. 8 |
|---|---|---|---|---|
| Phase A | | | | |
| Water | 67.52 | 67.17 | 64.97 | 67.22 |
| Disodium EDTA | 0.10 | 0.10 | 0.20 | 0.20 |
| Citric Acid | — | — | 1.40 | 1.40 |
| Sodium Laureth-3 Sulfate | 3.00 | 3.50 | — | — |
| Sodium Laureth-4 Carboxylate | 3.00 | 3.50 | — | — |
| Laureth-12 | 1.00 | 1.20 | — | — |
| Phase B | | | | |
| Polyquaternium 10 | — | — | 0.40 | 0.40 |
| Polyquaternium 25 | 0.30 | 0.30 | — | — |
| Glycerine | 3.00 | 3.00 | 3.00 | 3.00 |
| Phase C | | | | |
| Sodium Lauroamphoacetate | — | — | 6.00 | 6.00 |
| Lauric Acid | 6.00 | 6.00 | 3.00 | 3.00 |
| Myristic Acid | — | — | 3.00 | 3.00 |
| Magnesium Sulphate Hepta Hydrate | 2.30 | 2.00 | 2.00 | 2.00 |
| Triethanol Amine | 4.00 | 4.00 | 4.00 | 4.00 |
| Trihydroxystearin | 0.50 | 0.50 | 0.50 | 0.50 |
| Phase D | | | | |
| Sucrose Polyesters of Behenate Fatty Acid | 2.00 | 2.00 | 4.00 | 2.00 |
| Sucrose Polyesters of Cottonate Fatty Acid | 3.00 | 2.00 | — | — |
| PEG-6 Caprylic/Capric Triglycerides | — | — | — | 2.00 |
| Petrolatum | — | — | 4.00 | — |
| Mineral Oil | — | — | — | 2.00 |
| Phase E | | | | |
| Cocamidopropyl Betaine | 2.00 | 3.00 | 1.80 | 1.80 |

-continued

|  | Ex. 5 | Ex. 6 | Ex. 7 | Ex. 8 |
|---|---|---|---|---|
| Lauryl dimethyl amine oxide | 1.00 | 1.20 | 1.20 | 1.20 |
| Dex Panthenol | 1.00 | 0.25 | 0.25 | — |
| Phase F |  |  |  |  |
| DMDM Hydantoin | 0.08 | 0.08 | 0.08 | 0.08 |
| Fragrance | 0.20 | 0.20 | 0.20 | 0.20 |
|  | 100.00 | 100.00 | 100.00 | 100.00 |

The insoluble skin conditioning component of these compositions have an interfactial tension index of 150% or less.

Method of manufacture:

1. In a stainless steel vessel combine ingredients in phase A.
2. In a separate vessel combine ingredients in phase B until a homogeneous mixture is formed.
3. Add Phase B to phase A.
4. Add phase C ingredients to phase A vessel while heating to 85° C.
5. In a separate vessel, combine ingredients in phase D. Add to Phase A vessel.
6. Cool to 45° C. Add ingredients in phase E.
6. Continue cooling. When temperature reaches 30° C., add ingredients in phase F.

Examples 9–12

Shampoo

|  | Ex. 9 | Ex. 10 | Ex. 11 | Ex. 12 |
|---|---|---|---|---|
| Phase A |  |  |  |  |
| Water | 68.05 | 67.30 | 67.05 | 70.30 |
| Ammonium Lauryl Sulfate | 10.00 | 10.00 | 8.00 | 6.00 |
| Ammonium Laureth Sulfate | 4.00 | 3.00 | 2.00 | 2.00 |
| Cocamide MEA | 2.00 | 2.00 | 2.00 | 2.00 |
| Ethylene Glycol Distearate | 2.00 | 2.00 | 2.00 | 2.00 |
| Cetyl Alcohol | 2.00 | 2.00 | 2.00 | 2.00 |
| Stearyl Alcohol | 1.20 | 1.20 | 1.20 | 1.20 |
| Phase B |  |  |  |  |
| Glycerin | 1.00 | 1.00 | 1.00 | 1.00 |
| Polyquaternium 10 | 0.50 | 0.25 | — | — |
| Polyquaternium 24 | — | — | 0.50 | 0.25 |
| Phase C |  |  |  |  |
| Ammonium Lauryl Sulfate | 1.50 | 1.50 | 1.50 | 1.50 |
| Sodium Chloride | 0.10 | 0.10 | 0.10 | 0.10 |
| Sucrose Polyesters of Cottonate Fatty Acid | 3.00 | 3.00 | — | — |
| Sucrose Polyesters of Behenate Fatty Acid | 2.00 | 3.00 | 3.00 | 3.00 |
| Polydimethyl Siloxane | — | — | 3.00 | 2.00 |
| Phase D |  |  |  |  |
| Cocaminopropyl Betaine | — | 1.00 | 3.00 | 3.00 |
| Lauryl Dimethyl Amine Oxide | 1.50 | 1.50 | 1.50 | 1.50 |
| Decyl Polyglucose | — | — | 1.00 | 1.00 |
| Phase E |  |  |  |  |
| DMDM Hydantoin | 0.15 | 0.15 | 0.15 | 0.15 |
| Phenoxyethanol | 0.50 | 0.50 | 0.50 | 0.50 |
| Fragrance | 0.50 | 0.50 | 0.50 | 0.50 |
|  | 100.00 | 100.00 | 100.00 | 100.00 |

The insoluble skin conditioning component of these compositions have an interfactial tension index of 150% or less.

Method of manufacture:

1. In a stainless steel vessel combine ingredients in phase A.
2. In a separate vessel combine ingredients in phase B until a homogeneous mixture is foormed.
3. Add Phase B to phase A.
4. Heat to 70° C.
5. In a separate vessel, combine ingredients in phase C and mill for 45 minutes. Add to Phase A.
5. Cool to 45° C. Add ingredients in phase D.
6. Continue cooling. When temperature reaches 30° C., add ingredients in phase E.

What is claimed is:

1. A non-emulsified personal cleansing composition comprising:
    A. from about 35% to about 99.9%, by weight of the personal cleansing composition, of a cleansing component comprising:
        i. from about 5% to about 74.5%, by weight of the personal cleansing composition, of a lathering surfactant; and
        ii. from about 25% to about 94.9%, by weight of the personal cleansing composition, of water; and
    B. from about 0.1% to about 65%, by weight of the personal cleansing composition, of an insoluble skin conditioning component comprising:
        i. an insoluble skin conditioning solid; and
        ii. less than or equal to about 80%, by weight of the insoluble skin conditioning component, of an insoluble skin conditioning oil;
    wherein the insoluble skin conditioning component has an interfacial tension index of less than about 150% in the cleansing component.

2. A non-emulsified personal cleansing composition according to claim 1 wherein the insoluble skin conditioning component has an interfacial tension index of less than about 100% in the cleansing component.

3. A method of cleansing and conditioning the skin or hair comprising applying a safe and effective amount of the non-emulsified personal cleansing composition of claim 1 to the skin or hair of a human in need of such treatment.

4. A method of removing make-up from the skin comprising applying a safe and effective amount of the non-emulsified personal cleansing composition of claim 1 to the skin or hair of a human in need of such treatment.

5. A non-emulsified personal cleansing composition comprising:
    A. from about 35% to about 99.9%, by weight of the personal cleansing composition, of a cleansing component comprising:
        i. from about 5% to about 74.5%, by weight of the personal cleansing composition, of a lathering surfactant; and
        ii. from about 25% to about 94.9%, by weight of the personal cleansing composition, of water; and
    B. from about 0.1% to about 65%, by weight of the personal cleansing composition, of an insoluble skin conditioning component comprising:
        i. greater than or equal to about 20%, by weight of the insoluble skin conditioning component, of solid polyol carboxylic acid ester; and
        ii. less than or equal to about 80%, by weight of the insoluble skin conditioning component, of an insoluble skin conditioning oil;
    wherein the ratio of the amount of insoluble skin conditioning solid to the amount of insoluble skin conditioning oil is from about 20:80 to about 100:0; and wherein the insoluble skin conditioning component has an interfacial tension index of less than about 150% in the cleansing component.

6. A non-emulsified personal cleansing composition according to claim 5 wherein the solid polyol carboxylic acid ester is sucrose polyester in which the degree of esterification is 7–8, and in which the fatty acid moieties are $C_{18}$ mono- and/or di-unsaturated and behenic, in a molar ratio of unsaturates:behenic of 1:7 to 3:5.

7. A non-emulsified personal cleansing composition according to claim 6 wherein the solid polyol carboxylic acid ester is solid sugar polyester is the octaester of sucrose in which there are about 7 behenic fatty acid moieties and about 1 oleic acid moiety in the molecule.

8. A non-emulsified personal cleansing care composition according to claim 7 wherein the insoluble skin conditioning oil is a liquid polyol carboxylic acid ester.

9. A non-emulsified personal cleansing composition according to claim 5 wherein the insoluble skin conditioning oil is a liquid polyol carboxylic acid ester.

10. A non-emulsified personal cleansing composition according to claim 8 wherein the liquid polyol carboxylic acid ester is selected from the group consisting of cottonseed oil, soybean oil, fatty acid esters of sucrose, and mixtures thereof.

11. A non-emulsified personal cleansing composition according to claim 9 wherein the liquid polyol carboxylic acid ester is selected from the group consisting of cottonseed oil, soybean oil, fatty acid esters of sucrose, and mixtures thereof.

12. A non-emulsified personal cleansing composition comprising:
   A. from about 35% to about 99.9%, by weight of the personal cleansing composition, of a cleansing component comprising:
      i. from about 5% to about 74.5%, by weight of the personal cleansing composition, of a lathering surfactant; and
      ii. from about 25% to about 94.9%, by weight of the personal cleansing composition, of water; and
   B. from about 0.1% to about 65%, by weight of the personal cleansing composition, of an insoluble skin conditioning component comprising:
      i. greater than or equal to about 20%, by weight of the insoluble skin conditioning component, of a solid polyol carboxylic acid ester; and
      ii. less than or equal to about 80%, by weight of the insoluble skin conditioning component, of an insoluble skin conditioning oil;
   wherein the ratio of the amount of the solid polyol carboxylic acid ester to the amount of insoluble skin conditioning oil is from about 20:80 to about 100:0.

13. A non-emulsified personal cleansing composition according to claim 12 wherein the solid polyol carboxylic acid ester is sucrose polyester in which the degree of esterification is 7–8, and in which the fatty acid moieties are $C_{18}$ mono- and/or di-unsaturated and behenic, in a molar ratio of unsaturates:behenic of 1:7 to 3:5.

14. A non-emulsified personal cleansing composition according to claim 13 wherein the solid sucrose polyester is the octaester of sucrose in which there are about 7 behenic fatty acid moieties and about 1 oleic acid moiety in the molecule.

15. A non-emulsified personal cleansing composition comprising:
   A. from about 35% to about 99.9%, by weight of the personal cleansing composition, of a cleansing component comprising:
      i. from about 5% to about 74.5%, by weight of the personal cleansing composition, of a lathering surfactant; and
      ii. from about 25% to about 94.9%, by weight of the personal cleansing composition, of water; and
   B. from about 0.1% to about 65%, by weight of the personal cleansing composition, of an insoluble skin conditioning component comprising:
      i. greater than or equal to about 20%, by weight of the insoluble skin conditioning component, of a solid polyol carboxylic acid ester; and
      ii. less than or equal to about 80%, by weight of the insoluble skin conditioning component, of a liquid polyol carboxylic acid ester;
   wherein the ratio of the amount of the solid polyol carboxylic acid ester to the amount of insoluble skin conditioning oil is from about 20:80 to about 100:0.

16. A non-emulsified personal cleansing composition according to claim 15 wherein the solid polyol carboxylic acid ester is sucrose polyester in which the degree of esterification is 7–8, and in which the fatty acid moieties are $C_{18}$ mono- and/or di-unsaturated and behenic, in a molar ratio of unsaturates:behenic of 1:7 to 3:5.

17. A non-emulsified personal cleansing composition according to claim 16 wherein the solid polyol carboxylic acid ester is the octaester of sucrose in which there are about 7 behenic fatty acid moieties and about 1 oleic acid moiety in the molecule.

18. A non-emulsified personal cleansing composition according to claim 15 wherein the liquid polyol carboxylic acid ester is selected from the group consisting of cottonseed oil, soybean oil, fatty acid esters of sucrose, and mixtures thereof.

19. A non-emulsified personal cleansing composition according to claim 17 wherein the liquid polyol carboxylic acid ester is selected from the group consisting of cottonseed oil, soybean oil, fatty acid esters of sucrose, and mixtures thereof.

20. A non-emulsified personal cleansing composition comprising:
   A. from about 35% to about 99.9%, by weight of the personal cleansing composition, of a cleansing component comprising:
      i. from about 5% to about 74.5%, by weight of the personal cleansing composition, of a lathering surfactant; and
      ii. from about 25% to about 94.9%, by weight of the personal cleansing composition, of water; and
   B. from about 0.1% to about 65%, by weight of the personal cleansing composition, of an insoluble skin conditioning component comprising:
      i. greater than or equal to about 20%, by weight of the insoluble skin conditioning component, of the octaester of sucrose in which there are about 7 behenic fatty acid moieties and about 1 oleic acid moiety in the molecule; and
      ii. less than or equal to about 80%, by weight of the insoluble skin conditioning component, of a liquid polyol carboxylic acid ester selected from the group consisting of cottonseed oil, soybean oil, fatty acid esters of sucrose, and mixtures thereof;
   wherein the ratio of the amount of the octaester of sucrose to the amount of liquid polyol carboxylic acid ester is from about 20:80 to about 100:0.

21. A method of cleansing and conditioning the skin or hair comprising applying a safe and effective amount of the non-emulsified personal cleansing composition of claim 20 to the skin or hair of a human in need of such treatment.

22. A method of removing make-up from the skin comprising applying a safe and effective amount of the non-emulsified personal cleansing composition of claim 20 to the skin or hair of a human in need of such treatment.

* * * * *

UNITED STATES PATENT AND TRADEMARK OFFICE
CERTIFICATE OF CORRECTION

PATENT NO. : 5,916,575

DATED : June 29, 1999

INVENTOR(S) : David Michael McAtee et al.

It is certified that error appears in the above-identified patent and that said Letters Patent is hereby corrected as shown below:

On the title page, item [54] and column 1:

In the title "CLEANING" should read --CLEANSING--.

At column 6, line 11 "$R_2CO$—" should read --$R^2CO$—--.

Signed and Sealed this

Twenty-eighth Day of December, 1999

Attest:

Q. TODD DICKINSON

*Attesting Officer*  *Acting Commissioner of Patents and Trademarks*